United States Patent
Yi et al.

(10) Patent No.: US 12,076,588 B2
(45) Date of Patent: Sep. 3, 2024

(54) COMPENSATION METHOD FOR BED SURFACE DROP BEFORE AND AFTER ACCELERATOR RADIOTHERAPY BED

(71) Applicant: SUZHOU LINATECH MEDICAL SCIENCE AND TECHNOLOGY CO., LTD., Jiangsu (CN)

(72) Inventors: Jun Yi, Jiangsu (CN); Jonathan Yi Yao, Jiangsu (CN)

(73) Assignee: SUZHOU LINATECH MEDICAL SCIENCE AND TECHNOLOGY CO., LTD., Suzhou (CN)

( * ) Notice: Subject to any disclaimer, the term of this patent is extended or adjusted under 35 U.S.C. 154(b) by 267 days.

(21) Appl. No.: 17/786,459

(22) PCT Filed: Nov. 20, 2020

(86) PCT No.: PCT/CN2020/130425
§ 371 (c)(1),
(2) Date: Jun. 16, 2022

(87) PCT Pub. No.: WO2021/120983
PCT Pub. Date: Jun. 24, 2021

(65) Prior Publication Data
US 2023/0356002 A1 Nov. 9, 2023

(30) Foreign Application Priority Data
Dec. 19, 2019 (CN) .......................... 201911306945.5

(51) Int. Cl.
*A61N 5/10* (2006.01)
*G06F 17/18* (2006.01)

(52) U.S. Cl.
CPC ......... *A61N 5/1049* (2013.01); *A61N 5/1075* (2013.01); *G06F 17/18* (2013.01); *A61N 2005/1057* (2013.01)

(58) Field of Classification Search
CPC ................ A61N 5/1049; A61N 5/1075; A61N 2005/1057; G06F 17/18
See application file for complete search history.

(56) References Cited

U.S. PATENT DOCUMENTS

2016/0038115 A1  2/2016 Kosugi

FOREIGN PATENT DOCUMENTS

| CN | 105286905 A | 2/2016 |
| CN | 110270017 A | 9/2016 |

(Continued)

*Primary Examiner* — David P Porta
*Assistant Examiner* — Casey Bryant
(74) *Attorney, Agent, or Firm* — MUNCY, GEISSLER, OLDS & LOWE, P.C.

(57) ABSTRACT

A compensation method for bed surface drop before and after accelerator radiotherapy bed includes the following contents: the weight G is decomposed into N weights on average, the length L is decomposed into M positions on average, and then an experiment is carried out. The drop matrix $H_{N \times M}$ of the couch top is measured by the experiment, by performing cubic spline interpolation on the rows of the matrix $H_{N \times M}$, and then performing cubic spline interpolation on the columns, the resulting cubic spline interpolation matrix $S_{N \times N1, M \times M1}$ of $H_{N \times M}$ has N*N1 rows and M*M1 columns, and then applies it to practice. The drop amount H obtained by the compensation method for bed surface drop before and after accelerator radiotherapy bed of the present invention is the optimal estimated value with the Least Sum of Square Error.

9 Claims, 1 Drawing Sheet

(56) References Cited

FOREIGN PATENT DOCUMENTS

| CN | 106924886 A | 7/2017 |
| CN | 110385718 A | 10/2019 |
| CN | 111013027 A | 4/2020 |

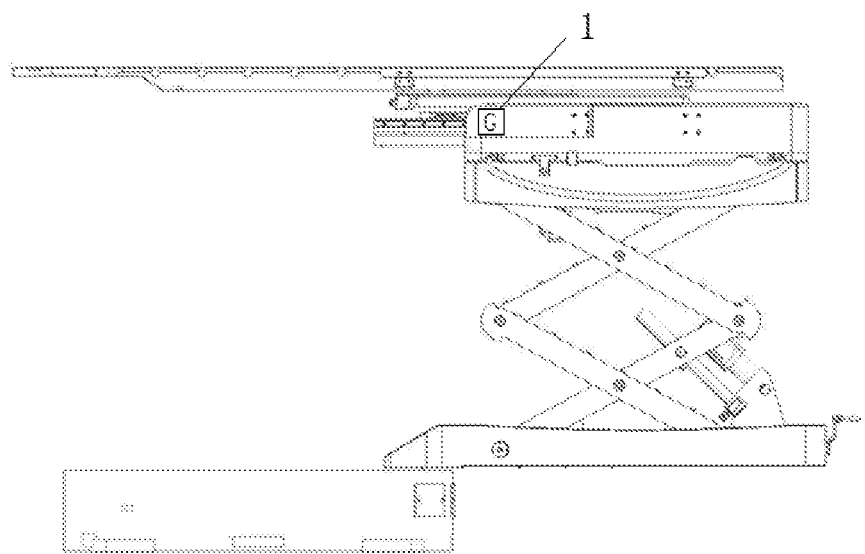

COMPENSATION METHOD FOR BED SURFACE DROP BEFORE AND AFTER ACCELERATOR RADIOTHERAPY BED

TECHNICAL FIELD

The invention belongs to the field of medical device of an accelerator radiation therapy couch, and particularly relates to the compensation method for bed surface drop before and after accelerator radiotherapy bed.

BACKGROUND

Radiation therapy is one of the main treatment methods for malignant tumors. With the use of many precision radiation therapy techniques in recent years, especially the wide application of IMRT, SRS and SBRT techniques, the accuracy of irradiation position has become the key to treatment. There are many aspects to cause the irradiation position error, such as changes in the patient's body, errors in operation and positioning, and elastic deformation of the treatment couch top under load. How to quickly correct the deviation through the mechanical device, especially the angle deviation of the treatment couch top, so as to achieve a more accurate placement is a problem we consider. The development trend of modern precision radiotherapy is to continuously improve the precision and accuracy of all aspects of radiotherapy, Image-guided radiotherapy technology (EPID, CBCT, dual-panel imaging system) can monitor the placement deviation of the internal target, requiring the accelerator treatment couch to be able to automatically correct online. Under normal circumstances, the positioning deviation is often in the six degrees of freedom directions, while the conventional treatment couch has only three linear motions in the three directions of X (front and back direction), Y (left and right direction), and Z (up and down direction) and the rotational movement of the treatment couch as a whole around the center of the class.

When the patient is lying on the treatment couch, as shown in FIG. 1, due to the patient's weight G and the couch top position L of moving the tumor to the isocenter position, at this time the couch top will drop down H due to gravity. The size of drop amount H is related to the patient's weight G and the couch top position L of moving the tumor to the isocenter position, ie, H=f(G,L), H is a two-dimensional nonlinear relationship between G and L.

There are two ways to solve this problem at this stage:
1. Install an angle sensor at the isocenter position of the couch top, move it to the isocenter position after the patient is lying down, and measure how much the angle of the couch has shifted. This method is theoretically feasible, but not feasible in practical applications. Because the angle sensor is in the isocenter position, it will be irradiated by X-rays, which will affect the normal operation and life of the angle sensor, and affect the X-ray image at the same time, causing shadows and interference to the image. It is also unfavorable for the treatment of patients, which will block the rays and affect the treatment.
2. Image-guided radiotherapy technology (EPID, CBCT, double-panel imaging system) can monitor the placement deviation of the internal target, so as to calculate the drop amount H. Due to the involvement of X-ray images, it will increase the patient's dose and will have certain impact for most of the normal tissue.

SUMMARY

In order to solve the above-mentioned technical problems, the present invention proposes a compensation method for bed surface drop before and after accelerator radiotherapy bed, which can obtain an accurate drop amount of the couch, so that the levelness of the treatment couch can be accurately corrected to ensure the actual treatment position is consistent with the planning treatment position to achieve the purpose of optimal treatment.

In order to achieve the above object, technical scheme of the present invention is as follows:

The compensation method for bed surface drop before and after accelerator radiotherapy bed includes the following steps:
S1: within the range of the patient's weight G, decompose G into N weights on average, that is $G=(G_1, G_2, \ldots, G_i, \ldots, G_N)$, within the range of the couch top position L of moving the tumor to the isocenter position, decompose L into M positions on average, that is $L=(L_1, L_2, \ldots, L_j, \ldots, L_M)$;
S2: carry out an experiment, under the condition of constant weight $G_i$ and length $L_j$, measure the drop amount $H_{ij}$ of the couch top through the experimental method to form a matrix $H_{N\times M}$, as shown below:

$$H = \begin{bmatrix} H_{11} & \ldots & H_{1j} & \ldots & H_{1M} \\ \vdots & \ldots & \vdots & \ldots & \vdots \\ H_{i1} & \ldots & H_{ij} & \ldots & H_{iM} \\ \vdots & \ldots & \vdots & \ldots & \vdots \\ H_{N1} & \ldots & H_{Nj} & \ldots & H_{NM} \end{bmatrix};$$

S3: in the case of a certain weight $G_i$, with $H(G_i,L_1)$, $H(G_i,L_2), \ldots, H(G_i,L_j), \ldots, H(G_i,L_M)$ as the calculation nodes, the cubic spline curve $S(G_i,L)$ of L is calculated by the cubic spline calculation method, the average subdivision between $L_{j-1}$ and $L_j$ is M1 parts, that is, $L_{j-1}, L_{j-1,1}, \ldots, L_{j-1,M1-1}, L_j$, and through the cubic polynomial $S(G_i,L)$, calculate $S(G_i,L_{j-1}), S(G_i,L_{j-1,1}), \ldots, S(G_i,L_{j-1,M1-1}), S(G_i,L_j);$ S4: in the case of a certain length $L_{j-1}, L_{j-1,1}, \ldots, L_{j-1,M1-1}$, $L_j$, with $H(G_1,L_{j-1,k})$, $H(G_2,L_{j-1,k})$, . . . , $H(G_i,L_{j-1,k}), \ldots, H(G_N,L_{j-1,k})$ as the calculation nodes, the cubic spline curve $S(G,L_{j-1,k})$ of L is calculated by the cubic spline calculation method, and the average subdivision between $G_{i+1}$ and $G_i$ is N1 parts, that is, $G_{i+1}, G_{i+1,1}, \ldots, G_{i+1,N1-1}, G_i$, and through $S(G,L_{j-1,k})$ cubic polynomial, calculate $S(G_{i+1},L_{j-1,k})$, $S(G_{i+1,1},L_{j-1,k})$, $S(G_{i+1,2},L_{j-1,k}), \ldots, S(G_{i+1,N},L_{j-1,k})$, $S(G_i,L_{j-1,k})$;
S5: for the experimental measurement value matrix $H_{N\times M}$, by performing cubic spline interpolation on rows, and then performing cubic spline interpolation on columns, the resulting cubic spline interpolation matrix $S_{N*N1, M\times M1}$ of $H_{N\times M}$ has N*N1 rows and M*M1 columns;
S6: the patient is lying on the treatment couch, and the actual weight G of the patient and the actual L of moving the tumor to the isocenter position are obtained, and the pixel point closest to the value is found, and the corresponding drop amount H is calculated by using this pixel point.

The drop amount H obtained by the compensation method for bed surface drop before and after accelerator radiotherapy bed of the present invention is the optimal estimated value with the Least Sum of Square Error.

On the basis of the above technical solutions, the following improvements can be made:

As a preferred solution, in step S2, under the condition that the weight $G_i$ and length $L_j$ are constant, the drop amount $H_{ij}$ of the couch top is measured by an optical distance indicator.

With the above preferred solution, the drop amount of the couch top is measured with an optical distance indicator, which is more convenient to operate.

As a preferred solution, the patient's weight G ranges from 5 to 150 kg.

As a preferred solution, the range of the couch top position L of moving the tumor to the isocenter position is 200 mm~1200 mm.

As a preferred solution, the steps of the cubic spline calculation method are as follows:
(1) calculate each value according to the determined conditions to form a system of equations;
(2) solve the system of equations to obtain M0, M1, M2, . . . , Mn;
(3) substitute the obtained value of Mi back into the expression of S(x), so that the approximate value S(x) of the function y=f(x) at any point can be obtained.

Using the above preferred solution, step (1) of the cubic spline calculation method is specifically:
set n+1 points on the given interval [a, b] a=x0< x1<x2< . . . <xn=b, and the corresponding function values yi=f(xi), i=0, 1, . . . , n;
if the function S(x) satisfies: in each subinterval [xk, xk+1](k=0, 1, . . . , n−1), S(x) is a polynomial of no more than three times, S(xi)=yi, i=0, 1, . . . , n; and S(x), S'(x), S"(x) are continuous on [a, b];
then S(x) is called the cubic spline interpolation function of f(x) on nodes x0, x1, x2, . . . , xn;
given n+1 sample points (xi, yi) (i=0, 1, . . . , n), determining a cubic spline interpolation function requires 4n independent conditions;

$$\begin{cases} S(x_0) = y_0, S(x_n) = y_n \\ S_-(x_i) = S_+(x_i) = y_i, \\ S'_-(x_i) = S'_+(x_i), \\ S''_-(x_i) = S''_+(x_i), \end{cases} (i = 1, 2, \ldots n-1)$$

$$S'(a) = f'(a), S'(b) = f'(b);$$

note $M_i = S''(x_i)$, the second derivative $S''(x)$ of $S(x)$ in $[x_i, x_{i+1}]$ is expressed as the following formula:

$$S''(x) = M_i \frac{x_{i+1} - x}{h_i} + M_{i+1} \frac{x - x_i}{h_i} \quad x \in [x_i, x_{i+1}],$$

wherein $h_i = x_{i+1} - x_i$.

As a preferred solution, step (2) of the cubic spline calculation method is specifically:
from the continuity S'(xi−)=S'(xi+), (i=1, 2, . . . , n−1) can get $$\mu_i M_{i-1} + 2M_i + \gamma_i M_{i+1} = d_i;$$

wherein $\begin{cases} \mu_i = \dfrac{h_{i-1}}{h_i + h_{i-1}}, \lambda_i = 1 - \mu_i \\ d_i = 6\left(\dfrac{y_{i+1} - y_i}{h_i} - \dfrac{y_i - y_{i-1}}{h_{i-1}}\right)(h_i + h_{i-1})^{-1} \end{cases};$ for Type 1 interpolation problems:

$$\lambda_0 = 1, d_0 = \frac{6\left[\frac{y_1 - y_0}{h_0} - y'_0\right]}{h_0};$$

$$\mu_n = 1, d_n = \frac{6\left[y'_n - \frac{(y_n - y_{n-1})}{h_{n-1}}\right]}{h_{n-1}};$$

when both G and L are uniformly divided:

$$\begin{cases} \mu_i = \frac{1}{2}, \gamma_i = \frac{1}{2} \\ d_i = 3(y_{i+1} - 2y_i + y_{i-1}) \end{cases};$$

$$\gamma_0 = 1, d_0 = 6(y_1 - y_0 - y'_0);$$

$$\gamma_n = 1, d_n = -6(y_n - y_{n-1} - y'_n);$$

the unknown parameters M0, M1, . . . , Mn can be solved by solving the following system of equations $$\begin{bmatrix} 2 & \lambda_0 & & & & \\ \mu_1 & 2 & \lambda_1 & & & \\ 0 & \mu_2 & 2 & \lambda_2 & & \\ & \ddots & \ddots & \ddots & & \\ & & & u_{n-1} & 2 & \lambda_{n-1} \\ & & & & \mu_n & 2 \end{bmatrix} \begin{bmatrix} M_0 \\ M_1 \\ M_2 \\ \vdots \\ M_{n-1} \\ M_n \end{bmatrix} = \begin{bmatrix} d_0 \\ d_1 \\ d_2 \\ \vdots \\ d_{n-1} \\ d_n \end{bmatrix}.$$

As a preferred solution, step (3) of the cubic spline calculation method is specifically:
substitute the parameters M0, M1, . . . , Mn into the expression S(x) to obtain the spline function:

$$S(x) = M_i \frac{(x_{i+1} - x)^3}{6h_i} + M_{i+1} \frac{(x - x_i)^3}{6h_i} + \left(\frac{y_i}{h_i} - \frac{M_i}{6} h_i\right)(x_{i+1} - x) + \left(\frac{y_{i+1}}{h_i} - \frac{M_{i+1}}{6} h_i\right)(x - x_i);$$

when h is normalized to 1, the above formula can be simplified as:

$$S(x) = M_i \frac{(x_{i+1} - x)^3}{6} + M_{i+1} \frac{(x - x_i)^3}{6} + \left(y_i - \frac{M_i}{6}\right)(x_{i+1} - x) + \left(y_{i+1} - \frac{M_{i+1}}{6}\right)(x - x_i);$$

wherein $x \in (x_i, x_{i+1})$.

As a preferred solution, a gravity sensor is provided on the treatment couch.

BRIEF DESCRIPTION OF THE DRAWINGS

FIG. 1 is a schematic structural diagram of an accelerator treatment couch provided by an embodiment of the present invention.

Where: 1—Gravity sensor.

DETAILED DESCRIPTION OF THE EMBODIMENTS

The preferred embodiments of the present invention will be described in detail below with reference to the accompanying drawings.

In order to achieve the purpose of the present invention, in some of the embodiments of the compensation method for bed surface drop before and after accelerator radiotherapy bed, The compensation method for bed surface drop before and after accelerator radiotherapy bed includes the following steps:

S1: within the range of the patient's weight G, decompose G into N weights on average, that is $G=(G_1, G_2, \ldots, G_i, \ldots, G_N)$, within the range of the couch top position L of moving the tumor to the isocenter position, decompose L into M positions on average, that is $L=(L_1, L_2, \ldots, L_j, \ldots, L_M)$;

S2: carry out the experiment, under the condition of certain weight $G_i$ and length $L_j$, measure the drop amount $H_{ij}$ of the couch top through the experimental method to form a matrix $H_{N \times M}$ (as shown in Table 1), as shown below:

$$H = \begin{bmatrix} H_{11} & \ldots & H_{1j} & \ldots & H_{1M} \\ \vdots & \ldots & \vdots & \ldots & \vdots \\ H_{i1} & \ldots & H_{ij} & \ldots & H_{iM} \\ \vdots & \ldots & \vdots & \ldots & \vdots \\ H_{N1} & \ldots & H_{Nj} & \ldots & H_{NM} \end{bmatrix};$$

S3: in the case of a certain weight $G_i$, with $H(G_i,L_1), H(G_i,L_2), \ldots, H(G_i,L_j), \ldots, H(G_i,L_M)$ as the calculation nodes, the cubic spline curve $S(G_i,L)$ of L is calculated by the cubic spline calculation method, and the average subdivision between $L_{j-1}$ and $L_j$ is M1 parts, that is, $L_{j-1}, L_{j-1,1}, \ldots, L_{j-1,M1-1}, L_j$, and through the $S(G_i,L)$ cubic polynomial, calculate $S(G_i,L_{j-1}), S(G_i,L_{j-1,1}), \ldots, S(G_i,L_{j-1,M1-1}), S(G_i,L_j)$; S4: in the case of a certain length $L_{j-1}, L_{j-1,1}, \ldots, L_{j-1,M1-1}, \ldots, L_j$, with $H(G_1,L_{j-1,k}), H(G_2,L_{j-1,k}), \ldots, H(G_i,L_{j-1,k}), \ldots, H(G_N,L_{j-1,k})$ as the calculation nodes, the cubic spline curve $S(G,L_{j-1,k})$ of L is calculated by the cubic spline calculation method, and the average subdivision between $G_{i+1}$ and $G_i$ is N1 parts, that is, $G_{i+1}, G_{i+1,1}, \ldots, G_{i+1,N1-1}, G_i$, and through $S(G,L_{j-1,k})$ cubic polynomial, calculate $S(G_{i+1},L_{j-1,k})$, $S(G_{i+1,1},L_{j-1,k}), S(G_{i+1,2},L_{j-1,k}), \ldots, S(G_{i+1,N-1},L_{j-1,k})$, $S(G_i,L_{j-1,k})$; S5: for the experimental measurement value matrix $H_{N \times M}$, by performing cubic spline interpolation on rows, and then performing cubic spline interpolation on columns, the resulting cubic spline interpolation matrix $S_{N \times N1, M \times M1}$ of $H_{N \times M}$ has $N*N1$ rows and $M*M1$ columns (It is equivalent to dividing the weight G into an average of $N*N1$ parts, and the length L into an average of $M*M1$ parts);

S6: the patient is lying on the treatment couch, the actual weight G of the patient and the actual L of moving the tumor to the isocenter position are obtained, and the pixel point closest to the value is found, and the corresponding drop amount H is calculated by using this pixel point.

The compensation method for bed surface drop before and after accelerator radiotherapy bed is also called the compensation method for drop of front and back couch top of accelerator treatment.

TABLE 1

Weight $G_i$(unit: Kg), Length $L_j$(unit: mm) And the measured value of the couch top drop (unit: mm)

| Weight(kg)/Length(mm) | 300 | 400 | 500 | 600 | 700 | 800 | 900 | 1000 | 1100 |
|---|---|---|---|---|---|---|---|---|---|
| 10 | 1.4 | 1.5 | 1.6 | 1.7 | 1.8 | 1.9 | 2 | 2.1 | 2.2 |
| 20 | 1.8 | 2 | 2.1 | 2.2 | 2.3 | 2.4 | 2.5 | 2.6 | 2.7 |
| 30 | 3 | 3.2 | 3.4 | 3.6 | 3.8 | 4 | 4.2 | 4.4 | 4.6 |
| 40 | 4 | 4.2 | 4.4 | 4.6 | 4.8 | 5 | 5.2 | 5.4 | 5.6 |
| 50 | 5 | 5.2 | 5.4 | 5.5 | 5.6 | 5.7 | 5.8 | 5.9 | 6.1 |
| 60 | 5.2 | 5.5 | 5.6 | 5.8 | 6 | 6.1 | 6.3 | 6.5 | 6.6 |
| 70 | 5.8 | 6 | 6.2 | 6.3 | 6.5 | 6.6 | 6.7 | 6.8 | 7 |
| 80 | 6.3 | 6.5 | 6.7 | 6.8 | 6.9 | 7 | 7.2 | 7.4 | 7.5 |
| 90 | 6.8 | 7 | 7.2 | 7.4 | 7.5 | 7.6 | 7.7 | 7.9 | 8 |
| 100 | 7.2 | 7.4 | 7.6 | 7.7 | 7.8 | 7.9 | 8 | 8.1 | 8.3 |
| 110 | 7.5 | 7.8 | 8 | 8.1 | 8.2 | 8.4 | 8.5 | 8.6 | 8.7 |
| 120 | 7.8 | 8 | 8.2 | 8.4 | 8.5 | 8.6 | 8.7 | 8.8 | 8.9 |
| 130 | 8 | 8.4 | 8.6 | 8.7 | 8.8 | 8.9 | 9 | 9.1 | 9.2 |
| 140 | 8.3 | 8.6 | 8.8 | 8.9 | 9 | 9.1 | 9.2 | 9.3 | 9.4 |

The drop amount H obtained by compensation method for bed surface drop before and after accelerator radiotherapy bed of the present invention is the optimal estimated value with the Least Sum of Square Error.

The present invention proposes a compensation method for bed surface drop before and after accelerator radiotherapy bed, which can obtain the precise drop amount of the couch, so that the levelness of the couch can be accurately corrected. It is ensured that the actual treatment position is consistent with the treatment position specified by the planning system, so as to achieve the purpose of optimal treatment.

In order to further optimize the implementation effect of the present invention, in other embodiments, other features and techniques are the same, the difference is that in step S2, under the condition of a certain weight $G_i$ and length $L_j$, the drop of the couch top $H_{ij}$ is measured by an optical indicator.

With the above preferred solution, the drop amount of the couch top is measured with an optical indicator, which is more convenient to operate. For example: in the original state (that is, when there is no patient and the couch top does not move forward, G=0, L=0), the laser is directed to the bottom of the couch top, and the drop amount H=0 of the couch top at this time is collected and recorded by the optical distance indicator.

When a weight-determined experimental object $G_i$ is placed on the couch top (or measured by a gravity sensor under the treatment couch) and the couch top is moved forward with the couch top position $L_j$, the drop amount H of the couch top is recorded by using an optical distance indicator.

Of course, the above is only one method of the experiment, and it is not the core idea of the present invention. The alternative methods can also be used to carry out the experiment to obtain the couch top drop amount H.

In order to further optimize the implementation effect of the present invention, other features and technologies are the same in other implementation methods, but the difference is that the patient's weight G ranges from 5 to 150 kg.

In order to further optimize the implementation effect of the present invention, other features and technologies are the same in other implementation methods, but the difference is that the range of the couch top position L of moving the tumor to the isocenter position is 200 mm~1200 mm.

Cubic Hermit interpolation has good smoothness. Since the 1960s, the so-called spline interpolation method was first developed due to the needs of engineering design such as aviation and shipbuilding. This kind of advantage improves the smoothness of the interpolation function, and is an interpolation algorithm with the least sum of squared errors. The spline interpolation method has become an extremely important branch of numerical approximation, and has been widely used in many fields.

The idea of spline interpolation: select appropriate low-order polynomials segment by segment, and connect them to form an interpolation function according to certain smoothness requirements.

In order to further optimize the implementation effect of the present invention, in other embodiments, other feature technologies are the same, the difference is that the steps of the cubic spline calculation method are as follows:

(1) calculate each value according to the determined conditions to form a system of equations;
(2) solve the system of equations to obtain M0, M1, M2, . . . , Mn;
(3) substitute the obtained value of Mi back into the expression of S(x), so that the approximate value S(x) of the function y=f(x) at any point can be obtained.

Using the above preferred solution, step (1) of the cubic spline calculation method is specifically:

Definition: set n+1 points on the given interval [a, b] a=x0<x1<x2<<xn=b, and the corresponding function value yi=f(xi), i=0, 1, . . . , n;

if the function S(x) satisfies: in each subinterval [xk, xk+1](k=0, 1, . . . ,n−1), S(x) is a polynomial of no more than three times, S(xi)=yi, i=0, 1, . . . , n; and S(x), S'(x), S"(x) are continuous on [a, b];

then S(x) is called the cubic spline interpolation function of f(x) on nodes x0, x1, x2, . . . , xn;

given n+1 sample points (xi, yi) (i=0, 1, . . . , n), determining a cubic spline interpolation function requires 4n independent conditions;

In the definition, 4n−2 conditions have been specified, namely $$\begin{cases} S(x_0) = y_0, S(x_n) = y_n \\ S_-(x_i) = S_+(x_i) = y_i, \\ S'_-(x_i) = S'_+(x_i), \\ S''_-(x_i) = S''_+(x_i), \end{cases} (i = 1, 2, \ldots n-1)$$

Therefore, it is generally necessary to specify two additional boundary conditions (type 1): the derivatives f(a) and f(b) of f(x) at both ends are known, and S'(a)=f'(a), S'(b)=f'(b);

Denote Mi=S"(xi), considering its form on any interval $[x_i, x_{i+1}]$, according to the definition of cubic spline, the second derivative S"(x) of S(x) is in each subinterval $[x_i, x_{i+1}]$ (i=0, 1, 2, . . . , n−1) are all linear functions;

therefore, the second derivative $[x_i, x_{i+1}]$ of S(x)=Si(x) is expressed as the following formula:

$$S''(x) = M_i \frac{x_{i+1} - x}{h_i} + M_{i+1} \frac{x - x_i}{h_i} \quad x \in [x_i, x_{i+1}],$$

wherein $h_i = x_{i+1} - x_i$.

As a preferred solution, step (2) of the cubic spline calculation method is specifically:

from the continuity S'(xi−)=S'(xi+), (i=1, 2, . . . , n−1) can get $$\mu_i M_{i-1} + 2M_i + \gamma_i M_{i+1} = d_i;$$

$$\text{wherein} \begin{cases} \mu_i = \frac{h_{i-1}}{h_i + h_{i-1}}, \lambda_i = 1 - \mu_i \\ d_i = 6\left(\frac{y_{i+1} - y_i}{h_i} - \frac{y_i - y_{i-1}}{h_{i-1}}\right)(h_i + h_{i-1})^{-1} \end{cases};$$

the solution to the Type 1 interpolation problem exists and is unique.

For Type 1 interpolation problems:

$$\lambda_0 = 1, d_0 = \frac{6\left[\frac{y_1 - y_0}{h_0} - y'_0\right]}{h_0};$$

$$\mu_n = 1, d_n = \frac{6\left[y'_n - \frac{(y_n - y_{n-1})}{h_{n-1}}\right]}{h_{n-1}};$$

when both G and L are uniformly divided:

$$\begin{cases} \mu_i = \frac{1}{2}, \gamma_i = \frac{1}{2} \\ d_i = 3(y_{i+1} - 2y_i + y_{i-1}) \end{cases};$$

$$\gamma_0 = 1, d_0 = 6(y_1 - y_0 - y'_0);$$

$$\gamma_n = 1, d_n = -6(y_n - y_{n-1} - y'_n);$$

the unknown parameters M0, M1, . . . , Mn can be solved by solving the following system of equations $$\begin{bmatrix} 2 & \lambda_0 & & & & \\ \mu_1 & 2 & \lambda_1 & & & \\ 0 & \mu_2 & 2 & \lambda_2 & & \\ & & \ddots & \ddots & \ddots & \\ & & & \mu_{n-1} & 2 & \lambda_{n-1} \\ & & & & \mu_n & 2 \end{bmatrix} \begin{bmatrix} M_0 \\ M_1 \\ M_2 \\ \vdots \\ M_{n-1} \\ M_n \end{bmatrix} = \begin{bmatrix} d_0 \\ d_1 \\ d_2 \\ \vdots \\ d_{n-1} \\ d_n \end{bmatrix}.$$

As a preferred solution, step (3) of the cubic spline calculation method is specifically:
substitute the parameters M0, M1, . . . , Mn into the S(x) expression to obtain the spline function:

$$S(x) = M_i \frac{(x_{i+1} - x)^3}{6h_i} + M_{i+1} \frac{(x - x_i)^3}{6h_i} + \left(\frac{y_i}{h_i} - \frac{M_i}{6} h_i\right)(x_{i+1} - x) + \left(\frac{y_{i+1}}{h_i} - \frac{M_{i+1}}{6} h_i\right)(x - x_i);$$

when h is normalized to 1, the above formula can be simplified as:

$$S(x) = M_i \frac{(x_{i+1} - x)^3}{6} + M_{i+1} \frac{(x - x_i)^3}{6} + \left(y_i - \frac{M_i}{6}\right)(x_{i+1} - x) + \left(y_{i+1} - \frac{M_{i+1}}{6}\right)(x - x_i);$$

wherein $x \in (x_i, x_{i+1})$.

As shown in FIG. 1, in order to further optimize the implementation effect of the present invention, in other embodiments, other features and technologies are the same, except that a gravity sensor 1 is provided on the treatment couch.

Using the above embodiment, a gravity sensor 1 is set on the treatment couch, the patient is lying on the couch, the gravity sensor directly measures the weight of the patient, and sends it to the processor. The processor obtains the precise drop amount according to the above-mentioned function, combined with the real-time L. Then, the compensation device can perform drop compensation according to the drop amount, thereby ensuring that the real treatment position is consistent with the planning treatment position to ensure the best treatment.

The invention provides a compensation method for bed surface drop before and after accelerator radiotherapy bed. Since H=f(G,L), and H is a two-dimensional nonlinear relationship between G and L, it is very difficult to establish their accurate mathematical models if the small-signal linearization method is used, because G and L need to be divided into small intervals. Therefore the workload is very heavy and inaccurate.

In the present invention, the corresponding relationship is approximated by a cubic spline function, and the cubic spline is an approximation algorithm with the least sum of squared errors. In the case of a certain weight $G_i$, to calculate the drop amount H at the position L, the cubic spline interpolation method can be used; in the case of a certain position $L_j$, to calculate the drop amount H at the weight G, the cubic spline interpolation method is also used. In this way, a more subdivided and more accurate H interpolation matrix can be obtained. Piece-wise linear interpolation has the advantages of simple calculation, good stability, guaranteed convergence and easy implementation on the computer.

Regarding the preferred embodiment of the present invention, it should be pointed out that for technician, without departing from the inventive concept of the present invention, several modifications and improvements can be made, which all belong to the protection scope of this present invention.

The invention claimed is:

1. A compensation method for bed surface drop before and after accelerator radiotherapy bed comprising the following steps:

S1: within the range of the patient's weight G, decompose G into N weights on average, that is $G=(G_1, G_2, \ldots, G_i, \ldots, G_N)$, within the range of the couch top position L of moving the tumor to the isocenter position, decompose L into M positions on average, that is $L=(L_1, L_2, \ldots, L_j, \ldots, L_M)$;

S2: carry out an experiment, under the condition of constant weight $G_i$ and length $L_j$, measure the drop amount $H_{ij}$ of the couch top through the experimental method to form a matrix $H_{N \times M}$, as shown below:

$$H = \begin{bmatrix} H_{11} & \ldots & H_{1j} & \ldots & H_{1M} \\ \vdots & \ldots & \vdots & \ldots & \vdots \\ H_{i1} & \ldots & H_{ij} & \ldots & H_{iM} \\ \vdots & \ldots & \vdots & \ldots & \vdots \\ H_{N1} & \ldots & H_{Nj} & \ldots & H_{NM} \end{bmatrix};$$

S3: in the case of a certain weight $G_i$, with $H(G_i,L_1)$, $H(G_i,L_2)$, \ldots, $H(G_i,L_j)$, \ldots, $H(G_i,L_M)$ as the calculation node, the cubic spline curve $S(G_i,L)$ of L is calculated by the cubic spline calculation method, and the average subdivision between $L_{j-1}$ and $L_j$ is M1 parts, that is, $L_{j-1}$, $L_{j-1,1}$, \ldots, $L_{j-1,M1-1}$, $L_j$, and through the cubic polynomial $S(G_i, L)$, calculate $S(G_i,L_{j-1}), S(G_i,L_{j-1,1}), \ldots, S(G_i,L_{j-1,M1-1}), S(G_i,L_j);$ S4: in the case of a certain length of $L_{j-1}$, $L_{j-1,1}$, \ldots, $L_{j-1,M1-1}$, $L_j$, with $H(G_1, L_{j-1,k})$, $H(G_2,L_{j-1,k})$, \ldots, $H(G_i,L_{j-1,k})$, \ldots, $H(G_N,L_{j-1,k})$ as the calculation node, the cubic spline curve $S(G,L_{j-1,k})$ of L is calculated by the cubic spline calculation method, and the average subdivision between $G_{i+1}$ and $G_i$ is N1 parts, that is, $G_{i+1}$, $G_{i+1,1}$, \ldots, $G_{i+1,N1-1}$, $G_i$, and through cubic polynomial $S(G,L_{j-1,k})$, calculate $S(G_{i+1},L_{j-1,k})$, $S(G_{i+1,1},L_{j-1,k})$, $S(G_{i+1,2},L_{j-1,k})$, \ldots, $S(G_{i+1,N-1},L_{j-1,k})$, $S(G_i,L_{j-1,k})$;

S5: for the experimental measurement value matrix $H_{N \times M}$, by performing cubic spline interpolation on the rows, and then performing cubic spline interpolation on the columns, the resulting cubic spline interpolation matrix $S_{N \times N1, M \times M1}$ of $H_{N \times M}$ has $N*N1$ rows and $M*M1$ columns;

S6: the patient is lying on the treatment couch, and the actual weight G of the patient and the actual L of moving the tumor to the isocenter position are obtained, and the pixel point closest to the value is found, and the corresponding drop amount H is calculated by using this pixel point.

2. The compensation method for bed surface drop before and after accelerator radiotherapy bed according to claim 1, wherein in the step S2, under the condition that weight $G_i$ and length $L_j$ are constant, the drop amount $H_{ij}$ of the couch top is measured by an optical distance indicator.

3. The compensation method for bed surface drop before and after accelerator radiotherapy bed according to claim 1, wherein the patient's weight G ranges from 5 to 150 kg.

4. The compensation method for couch top drop before and after accelerator radiotherapy bed according to claim 1, wherein the range of the couch top position L of moving the tumor to the isocenter position is 200 mm~1200 mm.

5. The compensation method for bed surface drop before and after accelerator radiotherapy bed according to claim 1, wherein the steps of the cubic spline calculation method are as follows:

(1) calculate each value according to the determined conditions to form a system of equations;

(2) solve the system of equations to obtain M0, M1, M2, \ldots, Mn;

(3) substitute the obtained value of Mi back into the expression of S(x), so that the approximate value S(x) of the function y=f(x) at any point can be obtained.

6. The compensation method for bed surface drop before and after accelerator radiotherapy bed according to claim 5, wherein the step (1) of the cubic spline calculation method is specifically:

set n+1 points on the given interval [a, b] a=x0< x1<x2< \ldots <xn=b, and the corresponding function values yi=f(xi), i=0,1, \ldots ,n;

if the function S(x) satisfies: in each subinterval [xk, xk+1](k=0,1, \ldots ,n-1), S(x) is a polynomial of no more than three times, S(xi)=yi, i=0,1, \ldots, n; and S(x), S'(x), S"(x) are continuous on [a, b];

then S(x) is called the cubic spline interpolation function of f(x) on nodes x0, x1, x2, \ldots, xn;

given n+1 sample points (xi, yi) (i=0, 1, ..., n), determining a cubic spline interpolation function requires 4n independent conditions;

$$\begin{cases} S(x_0) = y_0, S(x_n) = y_n \\ S_-(x_i) = S_+(x_i) = y_i, \\ S'_-(x_i) = S'_+(x_i), \\ S''_-(x_i) = S''_+(x_i), \end{cases} (i = 1, 2, \ldots n-1)$$

$$S'(a) = f'(a), S'(b) = f'(b);$$

note $M_i = S''(x_i)$, the second derivative $S''(x)$ of $S(x)$ in $[x_i, x_{i+1}]$ is expressed as the following formula:

$$S''(x) = M_i \frac{x_{i+1} - x}{h_i} + M_{i+1} \frac{x - x_i}{h_i} \quad x \in [x_i, x_{i+1}],$$

wherein $h_i = x_{i+1} - x_i$.

7. The compensation method for bed surface drop before and after accelerator radiotherapy bed according to claim 6, wherein the step (2) of the cubic spline calculation method is specifically:

from the continuity $S'(x_i-) = S'(x_i+)$, $(i=1, 2, \ldots, n-1)$ can get $$\mu_i M_{i-1} + 2M_i + \gamma_i M_{i+1} = d_i;$$

wherein $\begin{cases} \mu_i = \frac{h_{i-1}}{h_i + h_{i-1}}, \lambda_i = 1 - \mu_i \\ d_i = 6\left(\frac{y_{i+1} - y_i}{h_i} - \frac{y_i - y_{i-1}}{h_{i-1}}\right)(h_i + h_{i-1})^{-1} \end{cases};$ for Type 1 interpolation problems:

$$\lambda_0 = 1, d_0 = \frac{6\left[\frac{y_1 - y_0}{h_0} - y'_0\right]}{h_0};$$

$$\mu_n = 1, d_n = \frac{6\left[y'_n - \frac{(y_n - y_{n-1})}{h_{n-1}}\right]}{h_{n-1}};$$

when both G and L are uniformly divided:

$$\begin{cases} \mu_i = \frac{1}{2}, \gamma_i = \frac{1}{2} \\ d_i = 3(y_{i+1} - 2y_i + y_{i-1}) \end{cases};$$

$$\gamma_0 = 1, d_0 = 6(y_1 - y_0 - y'_0);$$

$$\gamma_n = 1, d_n = -6(y_n - y_{n-1} - y'_n);$$

the unknown parameters M0, M1, ..., Mn can be solved by solving the following system of equations $$\begin{bmatrix} 2 & \lambda_0 & & & & \\ \mu_1 & 2 & \lambda_1 & & & \\ 0 & \mu_2 & 2 & \lambda_2 & & \\ & & \ddots & \ddots & \ddots & \\ & & & \mu_{n-1} & 2 & \lambda_{n-1} \\ & & & & \mu_n & 2 \end{bmatrix} \begin{bmatrix} M_0 \\ M_1 \\ M_2 \\ \vdots \\ M_{n-1} \\ M_n \end{bmatrix} = \begin{bmatrix} d_0 \\ d_1 \\ d_2 \\ \vdots \\ d_{n-1} \\ d_n \end{bmatrix}.$$

8. The compensation method for bed surface drop before and after accelerator radiotherapy bed according to claim 7, wherein the step (3) of the cubic spline calculation method is specifically:

substitute the parameters M0, M1, ..., Mn into the expression $S(x)$ to obtain the spline function:

$$S(x) = M_i \frac{(x_{i+1} - x)^3}{6h_i} + M_{i+1} \frac{(x - x_i)^3}{6h_i} + \left(\frac{y_i}{h_i} - \frac{M_i}{6} h_i\right)(x_{i+1} - x) + \left(\frac{y_{i+1}}{h_i} - \frac{M_{i+1}}{6} h_i\right)(x - x_i);$$

when h is normalized to 1, the above formula can be simplified as:

$$S(x) = M_i \frac{(x_{i+1} - x)^3}{6} + M_{i+1} \frac{(x - x_i)^3}{6} + \left(y_i - \frac{M_i}{6}\right)(x_{i+1} - x) + \left(y_{i+1} - \frac{M_{i+1}}{6}\right)(x - x_i);$$

wherein $x \in (x_i, x_{i+1})$.

9. The compensation method for bed surface drop before and after accelerator radiotherapy bed according to claim 1, wherein the gravity sensor is provided on the treatment couch.

* * * * *